(12) United States Patent (10) Patent No.: US 7,498,473 B2
Zhou et al. (45) Date of Patent: Mar. 3, 2009

(54) PROCESS FOR DEHYDROCYCLODIMERIZATION

(75) Inventors: Lubo Zhou, Inverness, IL (US);
Benjamin J. Nagel, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 242 days.

(21) Appl. No.: 11/460,404

(22) Filed: Jul. 27, 2006

(65) Prior Publication Data

US 2008/0027254 A1   Jan. 31, 2008

(51) Int. Cl.
*C07C 2/76* (2006.01)
(52) U.S. Cl. .................... 585/417; 585/415
(58) Field of Classification Search ............ 585/415, 585/417
See application file for complete search history.

(56) References Cited

U.S. PATENT DOCUMENTS

| 4,520,118 A | 5/1985 | Gane et al. ............ 502/53 |
|---|---|---|
| 4,600,700 A | 7/1986 | McHale .................. 502/50 |
| 4,605,637 A | 8/1986 | Chang et al. ............ 502/64 |
| 4,654,455 A | 3/1987 | Chao .................... 585/415 |
| 4,724,271 A | 2/1988 | Martindale et al. ...... 585/415 |
| 4,746,763 A | 5/1988 | Kocal .................. 585/417 |
| 6,395,664 B1 | 5/2002 | Boehner et al. .......... 502/22 |
| 6,548,725 B2 | 4/2003 | Froment et al. ......... 585/653 |
| 6,657,096 B2 | 12/2003 | Boehner et al. ........ 585/418 |
| 2005/0059544 A1 | 3/2005 | Steigleder et al. ....... 502/208 |

FOREIGN PATENT DOCUMENTS

EP       0 485 683 B1   11/1990

OTHER PUBLICATIONS

U.S. Appl. No. 11/460,522, filed Jul. 27, 2006, Zhou et al.

*Primary Examiner*—Thuan Dinh Dang
(74) *Attorney, Agent, or Firm*—Maryann Maas

(57) ABSTRACT

This invention relates to a process for catalytic dehydrocyclodimerization wherein the reaction mixture contains from about 10 to about 200 wt. ppm water. Providing water in the reaction mixture allows for an extended life of the zeolitic catalyst thereby increasing the efficiency of the catalytic dehydrocyclodimerization process.

14 Claims, 2 Drawing Sheets

PROCESS FOR DEHYDROCYCLODIMERIZATION

FIELD OF THE INVENTION

The present invention relates to a process of dehydrocyclodimerization whereby the useful life of the catalyst is extended through the addition of water to the feed.

BACKGROUND OF THE INVENTION

Dehydrocyclodimerization is a process in which aliphatic hydrocarbons containing from 2 to 6 carbon atoms per molecule are reacted over a catalyst to produce a high yield of aromatics and hydrogen, with a light ends byproduct and a $C_2$-$C_4$ recycle product. This process is well known and is described in detail in U.S. Pat. Nos. 4,654,455 and 4,746,763 which are incorporated by reference. Typically, the dehydrocyclodimerization reaction is carried out at temperatures in excess of 500° C. (932° F.), using dual functional catalysts containing acidic and dehydrogenation components. The acidic function is usually provided by a zeolite which promotes the oligomerization and aromatization reactions, while a non-noble metal component promotes the dehydrogenation function. One specific example of a suitable catalyst is disclosed in U.S. Pat. No. 4,746,763 and consists of a ZSM-5 type zeolite, gallium and a phosphorus containing alumina as a binder.

The conditions used for the dehydrocyclodimerization reaction result in catalyst deactivation which is believed to be caused by excessive carbon formation (coking) on the catalyst surface. After several days (from about 3 to 10 depending on the operating temperature) enough activity has been lost due to coke deposition that regeneration of the catalyst is necessary. Regeneration involves burning or oxidizing the coke present on the catalyst at elevated temperatures. In addition to loss of activity due to coke formation, catalysts containing a phosphorus modified alumina as a binder are gradually deactivated (over a period of time from several months to about a year) by exposure to hydrogen at temperatures generally greater than 500° C. (932° F.) and particularly greater than 565° C. (1049° F.). This loss of activity due to hydrogen exposure, especially above 500° C. (932° F.), cannot be restored by regeneration means, i.e., burning or oxidation at elevated temperatures. Therefore, the catalyst may also be treated with a fluid comprising water and then dried as in U.S. Pat. No. 6,395,664 B1. As used in this application, regeneration refers to the process of restoring lost activity due to coke formation, while reactivation refers to the process of restoring lost activity due to hydrogen exposure.

Catalyst costs can be significant and extending the usable life of catalysts can amount to large savings. If an operator can use a batch of catalyst for a longer period of time before replacing the catalyst, the operator may experience significant costs savings over time through buying less catalyst. Also, each time the catalyst must cycle through regeneration and reactivation processes costs are incurred. So even with regeneration and reactivation processes, costs are best controlled by also increasing catalyst life. A process is needed which increases catalyst life and may be used in conjunction with known regeneration and reactivation processes. Preferably, the process should be easily incorporated and employed in both existing commercial catalytic dehydrocyclodimerization processes as well as those being designed.

Furthermore, increasing the activity of a catalyst may allow for a lesser quantity of catalyst to be required which in turn allows for a smaller reactor vessel thereby reducing capital and inventory expenditures. On the other hand, increasing the activity of a catalyst may allow for more feed to be processed using the same quantity of catalyst thereby increasing profitability. A process is needed which increases catalyst activity without decreasing selectivity or catalyst life.

SUMMARY OF THE INVENTION

The instant invention relates to a process for dehydrocyclodimerization wherein a zeolitic catalyst is contacted in a dehydrocyclodimerization zone at dehydrocyclodimerization conditions, with a reaction mixture comprising aliphatic hydrocarbons having from 2 to 6 carbon atoms per molecule and from about 10 to about 200 wt. ppm water, or a water precursor in an amount resulting in from about 10 to about 200 wt. ppm water, to generate an aromatic product stream. The zeolitic catalyst may comprise alumina containing phosphorus with a phosphorous content, ZSM-5 type zeolite, and gallium. The dehydrocyclodimerization conditions may include a temperature from about 350° C. to about 650° C. (662° F. to 1202° F.), a pressure from about 0 to about 300 psi(g) (0 to 2068 kPa(g)), and a liquid hourly space velocity from about 0.2 to about 5 $hr^{-1}$. The water precursor may be selected from the group consisting of alcohols, ethers, aldehydes, phenols, and ketones with specific examples including ethanol, methanol, butyl alcohol, dibutyl alcohol, and tertiary butyl alcohol.

To generate the reaction mixture, from about 10 to about 200 wt. ppm water, or a water precursor in an amount resulting in from about 10 to about 200 wt. ppm water, may be added to a feed fluid comprising aliphatic hydrocarbons having from 2 to 6 carbon atoms per molecule. The aliphatic hydrocarbons may be paraffins, olefins, or a mixture of both. The adding of the water or water precursor may be through using a liquid pump or vapor-vapor mixing. The water or water precursor may be added to the feed fluid, or when a multiplicity of reactors are employed, the water may be added to any or all of the interstage fluid mixtures.

In another embodiment of the invention, the feed fluid comprising aliphatic hydrocarbons having from 2 to 6 carbon atoms per molecule may be control dried so that the feed fluid contains from about 10 to about 200 wt. ppm water, or a water precursor in an amount resulting in from about 10 to about 200 wt. ppm water in order to generate the reaction mixture. Similarly, in yet another embodiment of the invention, the catalyst entering the reactor may be control dried so that the catalyst retains an amount of water or water precursor sufficient to provide all or part of the from about 10 to about 200 wt. ppm water in the reaction mixture. In other words, all or a part of the water required to result in from about 10 to about 200 wt. ppm water in the reaction mixture may be introduced to the reaction mixture via the catalyst that underwent controlled drying. Furthermore, the 10 to about 200 wt. ppm water in the reaction mixture may be achieved by a combination of water introduced with the catalyst and water introduced with the feed fluid.

DETAILED DESCRIPTION OF THE INVENTION

Figure 1:
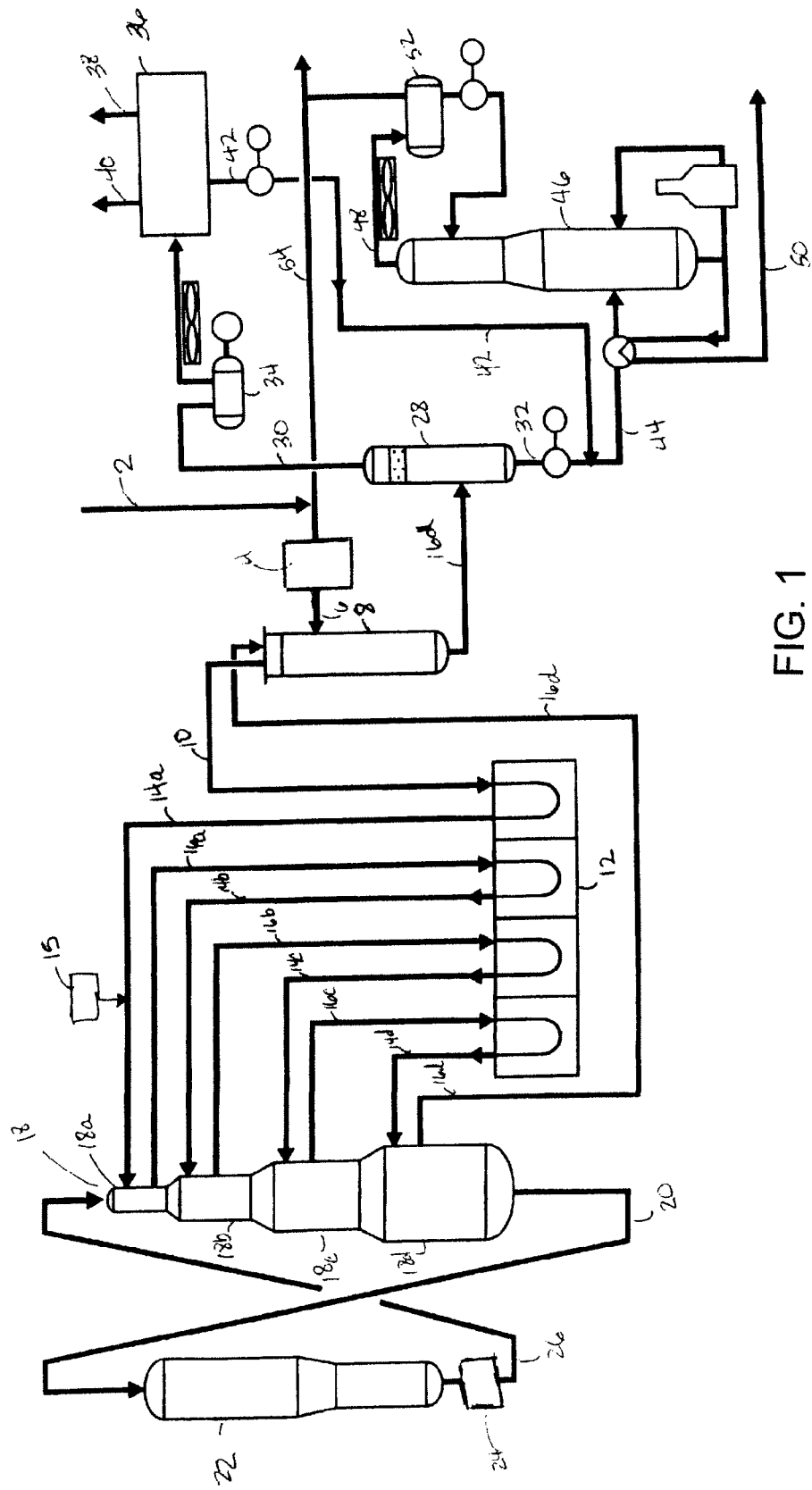
FIG. 1 shows a flow diagram of an embodiment of the invention.

As stated, this invention relates to a dehydrocyclodimerization process for preparing an aromatic stream from a light aliphatic hydrocarbon stream. The process uses a dehydrocyclodimerization catalyst which comprises a zeolite component, a binder component, and a gallium metal component. These catalysts are well known in the art and their preparation is also well known as shown by U.S. Pat. No. 4,629,717 which is incorporated by reference.

The zeolites which may be used are any of those which have a molar ratio of silicon (Si) per aluminum (Al) of greater than about 10 and preferably greater than 20 and a pore diameter of about 5 to 6 Angstroms. Specific examples of zeolites which can be used are the ZSM family of zeolites. Included among this ZSM family are ZSM-5, ZSM-8, ZSM-11, ZSM-12 and ZSM-35. The preparation of these ZSM-type zeolites is well known in the art and generally are prepared by crystallizing a mixture containing an alumina source, a silica source, an alkali metal source, water and a tetraalkyl ammonium compound or its precursor. The amount of zeolite present in the catalyst can vary considerably but usually is present in an amount from about 30 to about 90 weight percent and preferably from about 50 to about 70 weight percent of the catalyst.

A second component of the catalyst is a phosphorus containing alumina (hereinafter referred to as aluminum phosphate) component. The phosphorus may be incorporated with the alumina in any acceptable manner known in the art. One method of preparing this aluminum phosphate is that described in U.S. Pat. No. 4,629,717 which is incorporated by reference. The technique described in the '717 patent involves the gellation of a hydrosol of alumina which contains a phosphorus compound using the well-known oil drop method. Generally this technique involves preparing a hydrosol by digesting aluminum in aqueous hydrochloric acid at reflux temperatures of from about 80° C. (176° F.) to about 105° C. (221° F.). The ratio of aluminum to chloride in the sol ranges from about 0.7:1 to about 1.5:1 weight ratio. A phosphorus compound is now added to the sol. Preferred phosphorus compounds are phosphoric acid, phosphorous acid and ammonium phosphate. The relative amount of aluminum and phosphorus expressed in molar ratios of aluminum per phosphorus ranges from about 1:1 to 1:100 on an elemental basis.

The resulting aluminum phosphate hydrosol mixture is now gelled. One method of gelling this mixture involves combining a gelling agent with the mixture and then dispersing the resultant combined mixture into an oil bath or tower which has been heated to elevated temperatures such that gellation occurs with the formation of spheroidal particles. The gelling agents which may be used in this process are hexamethylenetetraamine, urea or mixtures thereof. The gelling agents release ammonia at the elevated temperatures which sets or converts the hydrosol spheres into hydrogel spheres. The spheres are then continuously withdrawn from the oil bath and typically subjected to specific aging treatments in oil and in ammoniacal solution to further improve their physical characteristics. The resulting aged and gelled particles are then washed and dried at a relatively low temperature of from about 93° C. to about 260° C. (200 to 500° F.) and heated in air at a temperature of from about 450° C. to about 816° C. (850-1500° F.) for a period of about 0.5 to about 20 hours. The amount of phosphorus containing alumina component present (as the oxide) in the catalyst can range from about 10 to about 70 weight percent and preferably from about 30 to about 50 weight percent.

The zeolite and aluminum phosphate binder are mixed and formed into particles by means well known in the art such as gellation, pilling, nodulizing, marumerizing, spray drying, extrusion or any combination of these techniques. One method of preparing the zeolite/aluminum phosphate support involves adding the zeolite either to an alumina sol or a phosphorus compound, forming a mixture of the alumina sol/zeolite/phosphorus compound which is now formed into particles by employing the oil drop method described above. The particles are heated in air as described above to give a support. Another method of preparing the zeolite/aluminum phosphate support involves adding the zeolite to water, adding an alumina sol to the zeolite-water mixture, and adding a phosphorous compound and a gelling agent while bead milling the alumina sol/zeolite/water mixture to form a mixture of alumina sol/zeolite/phosphorous compound/gelling agent/water. As described above, the mixture is oil dropped to form particles, which are heated in air to give the support.

Another component of the instant catalyst is a gallium component. The gallium component may be deposited onto the support in any suitable manner known to the art which results in a uniform dispersion of the gallium. Usually the gallium is deposited onto the support by impregnating the support with a salt of the gallium metal. The particles are impregnated with a gallium salt selected from the group consisting of gallium nitrate, gallium chloride, gallium bromide, gallium hydroxide, gallium acetate, etc. The amount of gallium which is deposited onto the support varies from about 0.1 to about 5 weight percent of the finished catalyst expressed as the metal.

The gallium compound may be impregnated onto the support particles by any technique well known in the art such as dipping the catalyst into a solution of the metal compound or spraying the solution onto the support. One preferred method of preparation involves the use of a steam jacketed rotary dryer. The support particles are immersed in the impregnating solution contained in the dryer and the support particles are tumbled therein by the rotating motion of the dryer. Evaporation of the solution in contact with the tumbling support is expedited by applying steam to the dryer jacket.

Next, the particles are heated in air and steam at a temperature of about 300° C. to about 800° C. (572° F. to 1472° F.) for a time of about 1 to about 10 hours. The amount of steam present in the air varies from about 1 to about 40 percent. Alternatively, the particles may be heated in air and steam in a two step process. In the first step, the particles are heated in air at a temperature of from about 316° C. to about 427° C. (600° F. to 800° F.) for a time of from about 0.5 to about 1 hr with no added steam, but with steam present in the air from about 10 to about 40 percent as a result of water vaporizing from the particles. In the second step, the particles are heated in air and steam at a temperature of from about 552° C. to about 663° C. (1025° F. to 1225° F.) for a time of about 1 to about 2 hr, with steam added in order to maintain about 5 to about 20 percent steam in the air. Either the one-step method or the two-step method provides a catalyst with well dispersed gallium.

In another embodiment, the catalyst may be heated under a hydrogen atmosphere at a temperature of about 500° C. to about 700° C. for a time of about 1 to about 15 hours. Although a pure hydrogen atmosphere best reduces and disperses the gallium, the hydrogen may be diluted with nitrogen. Alternatively, the reduction and dispersion can be done in situ in the actual reactor vessel used for dehydrocyclodimerization by using with either pure hydrogen or a mixture of hydrogen and hydrocarbons. Next the hydrogen treated particles are heated in air and steam at a temperature of about 400 to about 700 C for a time of about 1 to about 10 hours. The amount of steam present in the air varies from about 1 to about 40 percent.

It is preferred that the catalysts be treated with an aqueous solution of a weakly acidic ammonium salt or a dilute acid solution. The purpose of this treatment is to maximize both fresh catalyst activity and the resistance of the catalyst to deactivation caused by exposure to hydrogen. The ammonium salts which can be used include ammonium chloride, ammonium acetate, ammonium nitrate and mixtures thereof. The total concentration of these salts can vary from about 0.1 to about 5 molar. The acids which can be used include hydrochloric, acetic, nitric and sulfuric acid. Although concentrated acids could be used, they would degrade the zeolite and the integrity of the particles as well as removing the undesirable aluminum phosphorus species. It is desirable to use dilute acids which have a molarity of generally from about 0.001 to about 5 moles/liter and preferably from about 0.001 to about 1 moles/liter. Thus, in another aspect of this invention, it has been found that an increase in resistance to hydrogen deactivation in a catalyst can be achieved by using an acid treatment solution having a molarity lower than the minimum molarity of 0.1 moles/liter used in the prior art. Of these treatment solutions, it is preferred to use an ammonium nitrate solution. The treating solution is contacted with the catalyst particles that at a temperature of about 50° C. to about 100° C. (122° F. to 212° F.) for a time of about 1 to about 48 hours. After this treatment, the particles are separated from the aqueous solution, dried and heated in air at a temperature of about 500° C. to about 700° C. (932° F. to 1292° F.) for a time of about 1 to about 15 hours, thereby providing a catalyst that can be used in a dehydrocyclodimerization process of instant invention.

The dehydrocyclodimerization conditions which are employed vary depending on such factors as feedstock composition and desired conversion. A desired range of conditions for the dehydrocyclodimerization of $C_2$-$C_6$ aliphatic hydrocarbons to aromatics include a temperature from about 350° C. to about 650° C. (662° F. to 1202° F.), a pressure from about 0 to about 300 psi(g) (0 to 2068 kPa(g)), and a liquid hourly space velocity from about 0.2 to about 5 $hr^{-1}$. One embodiment of the invention employs process conditions including a temperature in the range from about 400° C. to about 600° C. (752° F. to 1112° F.), a pressure in or about the range from about 0 to about 150 psi(g) (0 to 1034 kPa(g)), and a liquid hourly space velocity of between 0.5 to 3.0 $hr^{-1}$. It is understood that, as the average carbon number of the feed increases, a temperature in the lower end of the temperature range is required for optimum performance and conversely, as the average carbon number of the feed decreases, the higher the required temperature.

The feed stream to the dehydrocyclodimerization process is defined herein as all streams introduced into the dehydrocyclodimerization reaction zone. Included in the feed stream is the $C_2$-$C_6$ aliphatic hydrocarbons. By $C_2$-$C_6$ aliphatic hydrocarbons is meant one or more open, straight or branched chain isomers having from two to six carbon atoms per molecule. Furthermore, the hydrocarbons in the feedstock may be saturated or unsaturated. Preferably, the hydrocarbons are $C_3$'s and/or $C_4$'s selected from isobutane, normal butane, isobutene, normal butene, propane and propylene. Diluents may also be included in the feed stream. Examples of such diluents include nitrogen, helium, argon, neon.

Additionally, in one embodiment of the invention the feed stream contains from about 10 to about 200 wt. ppm of water or at least one water precursor that results in from about 10 to about 200 wt. ppm water in the feed. In one embodiment, the water in the feed stream is from about 10 to about 100 wt. ppm or a suitable amount of water precursor is added to the feed stream to result in from about 10 to about 100 wt. ppm water. A water precursor, or oxygenate, such as alcohol, ether, ester, aldehyde, phenol, or some ketones may be added to the reaction mixture instead of water because at reaction conditions and in the presence of an acidic catalyst the oxygenate will undergo dehydration or other reactions to form water. Alcohols, ethers, and phenols readily undergo dehydration to form water, and aldehydes and ketones may undergo other reactions such as aldol condensation or various other decomposition reactions to ultimately form water.

Any water precursor that will undergo sufficient dehydration or degradation at the reaction conditions would be suitable for use in the invention. Enough water precursor should be added so that the product water formed in the reaction mixture is in the desired concentration range as discussed above. Given the operating conditions of the process and the exact identity of the catalyst and water precursor, one skilled in the art would be able to readily determine how much water precursor to add to generate a particular amount of water. Examples of suitable alcohols and ethers include those containing from about 1 to about 8 carbon atoms, depending upon the reaction temperature. Particularly preferred alcohols are ethanol, methanol, butyl alcohol, dibutyl alcohol, or tertiary butyl alcohol. The reaction temperature should be about 80° C. for the dehydration to occur. This approach of adding a water precursor instead of water to the reaction mixture may be commercially preferred, since the water precursor is apt to be more miscible with a hydrocarbon feedstock than water would be. Also, since the water precursor will have a greater molecular weight than water, it may be easier to physically add the correct amount of the water precursor to the reaction mixture than it would be to add the correct amount of water. For simplicity, the discussion herein will be in terms of water with the understanding the water precursors are also suitable.

The water or water precursor may be introduced to the reaction mixture in a variety of different ways known in the art. Examples of techniques suitable to add water or water precursors to the feed stream include vapor-vapor mixing prior to the reaction zone, employing at least one liquid pump to inject fluid into the feed stream, interstage liquid injection, and interstage mixing. Of course, the interstage liquid injection and the interstage mixing are options when the reaction zone contains more than one reaction vessel. The water or water precursor may be injected directly into the reactor to mix with the reaction mixture.

In another embodiment, the drying of the catalyst that is loaded into the reaction zone may be controlled so that some or all of the water required in the dehydrocyclodimerization process is retained on the catalyst which is placed in the reaction zone. The amount of water that is provided to the reaction mixture via the catalyst need not be added to the feed stream. Whether the water or a water precursor is introduced via the catalyst, via the feed, or a combination of both, the reaction mixture contains from about 10 to about 200 wt. ppm of water or from about 10 to about 100 wt. ppm water. Where only a portion of the required water is present on the catalyst, and the feed stream contains no water, the balance may be added to the feed stream as discussed above.

Similarly, the feed stream may pass through one or more dryers before reaching the dehydrocyclodimerization process. If so, the dryer(s) may be controlled so that if the feed stream contained water or water precursor(s) the dryer would remove only that amount in excess of the desired amount of water or water precursor(s) for the dehydrocyclodimerization process. If additional water or water precursor is needed to reach the desired range, it may be added as discussed above. The required amount of water may be reached through a combination of controlling the drying of the feed stream and controlling the drying of the catalyst.

The water present in the reaction mixture provides several key benefits. Often, the catalyst is periodically regenerated by burning coke from a continuous regeneration unit. After regeneration, the catalyst losses some activity, and the operating temperature must be increased to achieve the same level of conversion. Water addition to the feed or reaction mixtures changes the way in which the unit is operated thereby extending the life of the catalyst. For example, since catalyst activity is higher in the presence of water, the start-of-run temperature can be lowered and yet still achieve the same required conversion. The end-of-run temperature is generally a fixed parameter. In this way, the overall temperature window from start-of-run to end-of-run increases. With a larger window of temperature, more regeneration cycles may be completed before the operational temperature required by the regenerated catalyst becomes too great. More cycles allows the existing catalyst to remain in service for a longer period of time before a reload of fresh catalyst is required. In another example, the residence time of the catalyst in the reactor can be increased due to high activity and slow coke deactivation. Again, with a larger window of temperature available the catalyst may remain on-line for a longer period of time before regeneration is necessary thus increasing the catalyst life. Or, in other words, the regeneration frequency is reduced, hence, catalyst life extends.

When designing a unit according to the present invention, the process unit may be designed for a lesser amount of required catalyst as compared to typical process units today. The activity increase from water injection results in a lesser amount of catalyst required to perform the same level of operation. Costs associated with purchasing catalyst would be reduced and capital costs would be reduced since smaller scale equipment would be sufficient for the reduced amount of catalyst. If the same amount of the catalyst were to be maintained as compared to typical units today and the same scale of equipment were to be maintained, an increased amount of feed could be processed at the same amount of catalyst loaded. The result would be more product generated by the same size of unit.

When water itself and not a water precursor is used, due to the operating conditions of the dehydrocyclodimerization reactor, the water will be in the vapor state when contacting the catalyst. However, when the water is first introduced into the feed stream, the water can be in the liquid state, and or in the vapor state in the form of steam. It is believed that the source of the water is not critical to the success of this invention. Accordingly, reagent grade water is believed to be suitable for the fluid water. An example of reagent grade water is American Chemical Society CAS Number 7732-18-5, which is available from Aldrich, Milwaukee, Wis., USA. Suitable fluid water is not limited to reagent grade water, however. The source of the fluid water may be water that has a concentration of a salt or of an acid that is greater than 0.1 moles per liter and that has been processed to decrease the concentration to less than 0.1 moles per liter. Such processing includes distillation optionally followed by condensation, and also includes deionization. By deionization it is meant the removal by ion exchange from the water of at least a portion of its cations such as sodium, magnesium, and calcium, or of its anions such sulfates, carbonates, and nitrates. Ions may deposit on the catalyst and cause deleterious affects on the performance of the catalyst. Preferably, the water has also been processed to remove solids, such as by filtration or by reverse osmosis. Solids may deposit on the catalyst and adversely affect catalytic performance also. As an alternative to water in the liquid state or in the vapor state, a liquid-vapor mixture of liquid water and steam may be added to the feed.

The reaction mixture containing water is contacted with the catalyst in a dehydrocyclodimerization reaction zone maintained at dehydrocyclodimerization conditions. The catalyst may be in a fixed bed system, a moving bed system, a fluidized bed system, or in a batch type operation; however, in view of the danger of attrition losses of the valuable catalyst and of the well-known operational advantages, it is preferred to use either a fixed bed system or a dense-phase moving bed system such as shown in U.S. Pat. No. 3,725,249.

In a fixed bed system or a dense-phase moving bed system, the feed stream is preheated by any suitable heating means to the desired reaction temperature and then passed into a dehydrocyclodimerization zone containing a bed of catalyst. It is understood that the dehydrocyclodimerization zone may be one or more separate reactors with suitable means between separate reactors if any to compensate for any endothermicity encountered in each reactor and to assure that the desired temperature is maintained at the entrance to each reactor. It is also important to note that the feed stream may be contacted with the catalyst bed in either upward, downward, or radial flow fashion with the latter being preferred. In addition, the feed stream is in the vapor phase when its' components contact the catalyst bed. Each reactor may contain one or more fixed or dense-phase moving beds of catalyst. The dehydrocyclodimerization system preferably comprises a dehydrocyclodimerization zone containing one or more reactors and/or beds of catalyst. In a multiple bed system, it is, of course, within the scope of the present invention to use one catalyst in less than all of the beds with another dehydrocyclodimerization or similarly behaving catalyst being used in the remainder of the beds. Specific to the dense-phase moving bed system, it is common practice to remove catalyst from the bottom of a reactor in the dehydrocyclodimerization zone, regenerate it by conventional means known to the art, and then return it to the top of that reactor or another reactor in the dehydrocyclodimerization zone. After some time on stream (several days to a year), the catalyst described above will have lost enough activity due to coking and hydrogen exposure so that it must be reactivated. It is believed that the exact amount of time which a catalyst can operate without necessitating regeneration or reactivation will depend on a number of factors. One factor, as is demonstrated herein is whether water is added to the feed stream.

When the catalyst requires regeneration, typically oxidation or burning of catalyst deactivating carbonaceous deposits with oxygen or an oxygen-containing gas is used. Catalyst regeneration techniques are well known and not discussed in detail here. Examples include U.S. Pat. No. 4,795,845 (hereby incorporated by reference) which discloses burning the coke accumulated upon the deactivated catalyst at catalyst regeneration conditions in the presence of an oxygen-containing gas, and U.S. Pat. No. 4,724,271 (hereby incorporated by reference) which additionally discloses water removal steps in the catalyst regeneration procedure. The regeneration may proceed in one or multiple burns. For example, there may be a main burn followed by a clean-up burn. The main burn constitutes the principal portion of the regeneration process with the clean-up burn gradually increasing the amount of molecular oxygen in the gas introduced to the regeneration catalyst until the end of the clean-up burn which is indicated by a gradual decline in the temperature at the edit of the catalyst bed until the inlet and outlet temperatures of the catalyst bed merges.

Similarly, when the catalyst requires reactivation, it is removed from the operating reactor and contacted with fluid water. Suitable reactivation processes are known and not discussed in detail here. One example is U.S. Pat. No. 6,395,644. Using procedures in the art, the catalyst can be reactivated multiple times. Thus, the catalyst can be hydrogen deactivated, then reactivated, then hydrogen deactivated again, then reactivated again and so forth. No limit on the number of times that a particular catalyst can be deactivated and subsequently reactivated is known. The application and use of additional required items are well within the purview of a person of ordinary skill in the art. U.S. Pat. Nos. 3,652,231; 3,647,680; and 3,692,496; which are incorporated by reference into this document, may be consulted for additional detailed information.

Turning to FIG. 1, which is a simplified block flow diagram of the invention, fresh feed 2 and recycle 54 are combined and passed through drier 4. In one embodiment of the invention, drier 4 is controlled so that all or part of the 10 to 200 wt. ppm of the water in the reaction mixture was introduced via the drier effluent 6. Note that other water precursors may be used in lieu of water as discussed above. For purposes of illustration the invention will be discussed with respect to FIG. 1 in terms of the embodiment were water is the material being added to or controlled within the system. In another embodiment of the invention, drier 4 is controlled so that drier effluent 6 contains virtually no water. In yet another embodiment of the invention, only fresh feed 2 or recycle 54 is passed through drier 4 which may be controlled to either dry the fluid as much as possible, or provide all or a part of the desired amount of water in the reaction mixture. Moisture measurements may be performed on each of the streams to control and monitor the amount of water in the streams and thus the amount of water in the reaction mixture. Drier effluent 6 is passed through combined heat exchanger 8 and the partially heated stream 10 is passed to fired heaters 12 for additional heating to reach reaction temperature. The heated fluid feed in line 14a is passed to the dehydrocyclodimerization reactor stack 18 which is comprised of four adiabatic radial flow reactors arranged in a vertical stack 18a, 18, 18c, and 18d. Catalyst flows vertically by gravity down the stack and the fluid flows radially across the annular catalyst beds, between each reactor 18a-d, the fluid is passed through lines 14b-d and 16a-16c to and from fired heater 12 for interstage heating. If the feed fluid was dried in drier 4 to contain virtually no water, water may be added to any of the input lines 14a-14d to reactor stack 18, or to the interstage output lines 16a-16c. Water may be added via optional device(s) 15 where the devices may be a liquid injector pump or a vapor-vapor mixer. Only one stream 14a-14d or 16a-16c may be equipped with a corresponding device 15, each stream may be equipped with its' own device 15, or any combination of streams may be so equipped. The figure shows only stream 14a having a device 15 which is preferably a liquid injection pump.

The effluent from last reactor 18d is passed in line 16d though combined heat exchanger 8 to product separator 28 where the effluent is split into vapor product 30 and liquid product 32. Liquid product 32 is mixed with recycle stream 42 from gas recovery section 36 to form combined liquid product 44 which is sent to stripper 46. In stripper 46 light saturates are removed in stripper overhead 48 and the C6+ aromatic product is removed in stripper bottoms 50. Stripper overhead 48 is passed through overhead receiver 52 and recycle 54 is generated. Vapor product 30 is condensed and sent to gas recovery section 36. A stream 40 of approximately 95% hydrogen is removed from gas recovery section 36, as is a fuel gas stream 38 of light saturates and a recycle stream 42.

Coke builds up of the catalyst over time at reaction conditions and partially deactivated catalyst is continually withdrawn from the bottom of the reactor stack in line 20 for regeneration in vessel 22. In vessel 22, accumulated carbon is burned off. Regenerated catalyst is removed in line 26 and conducted to reactor stack 18. A drier is typically part of the regeneration zone as part of the regeneration process. In one embodiment of the invention, the drier of the catalyst regeneration zone is equipped with a controller to form a controlled drier 24. Controlled drier 24 is controlled to only partially dry the catalyst and leave some water or a water precursor on the catalyst. All or part of the 10 to 200 wt. ppm water of the reaction mixture may be provided by water or water precursor retained on the catalyst. The water retained on the catalyst provides water to the reaction mixture to achieve the benefits listed herein. It is within the scope of the invention that optional drier 24 may be used in combination with optional drier 4 and or device(s) 15 in any combination to achieve the desired amount of water in the reaction mixture in reactor stack 18.

The following example is presented to illustrate this invention and is not intended as an undue limitation on the generally broad scope of the invention as set out in the appended claims.

EXAMPLE 1

A comparative test was performed to demonstrate the benefit of utilizing water or a water precursor in the feed stream to a dehydrocyclodimerization process to increase catalyst life. In all runs of the test, the dehydrocyclodimerization unit was operated in the same manner. The feed entered the dehydrocyclodimerization reaction zone which operated at an average temperature of 540° C., a pressure of 15 psig (103 kPag) and a liquid hourly space velocity of $1.1\, hr^{-1}$. In all runs of the test, the dehydrocyclodimerization reaction zone contained a gallium-modified zeolitic catalyst bound with alumina containing phosphorus. A single batch of the same catalyst was divided into three portions. In runs B and C, the catalyst was employed in the "as received" basis, meaning the catalyst was dried before use, but no other treatments were employed. In run A, the catalyst was steamed in a laboratory before being loaded into the reactor.

Three runs of the test were completed and the results compared. The first run, A, used a propane feed stream. The second run, B, used the same propane feed stream with the addition of sufficient tertiary butyl alcohol to result in 40 wt. ppm water in the feed stream and a third run, C, used the same propane feed stream with the addition of sufficient tertiary butyl alcohol to result in 100 wt. ppm water in the feed stream. Through contact with the catalyst at dehydrocyclodimerization reaction conditions, the propane feed stream was converted into an aromatic hydrocarbon-containing product.

Figure 2:
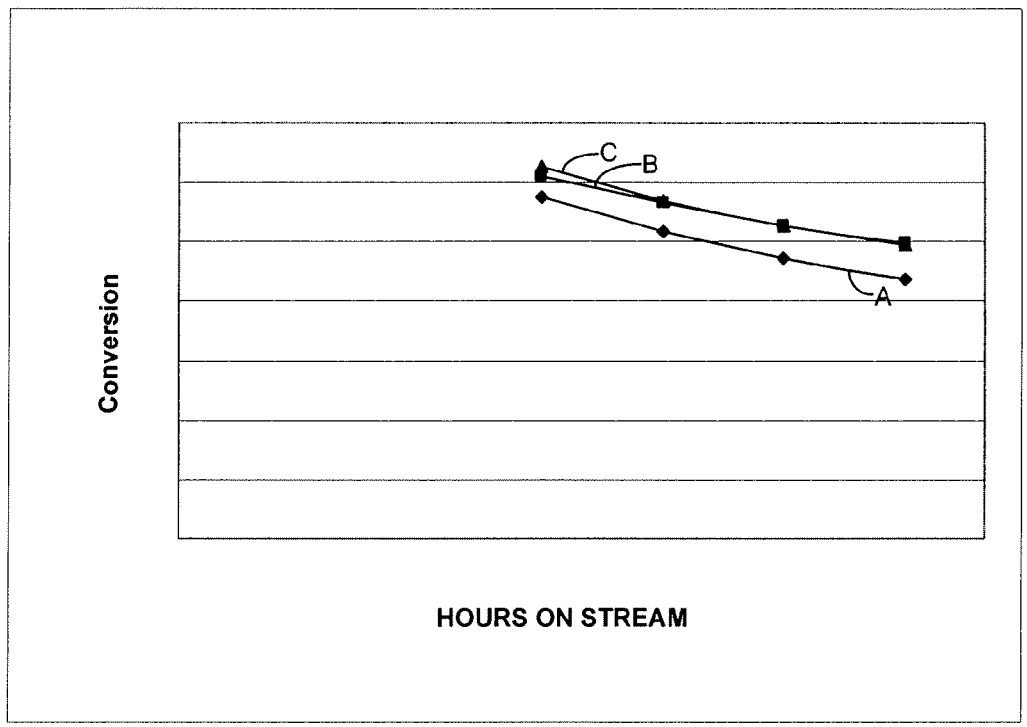
FIG. 2 is a plot of the conversion of propane as a function of time on stream as determined in comparative test runs of the Example.

The results of the three runs are in FIG. 2 which shows the conversion of propane as a function of time on stream. Runs B and C, the tests with added water to the feed stream, clearly show a higher conversion than the run A which had no water added to the feed. Comparing runs B and C, it is clear that the conversions were quite similar to one another while run A showed conversions that were notably less than runs B and C. The runs where either 40 wt. ppm or 100 wt. ppm of water was added to the feed fluid showed considerably higher conversion of the propane as compared to run A which had no water in the propane feed. The two runs with added water in the feed, Runs B and C showed very similar results.

Figure 3:
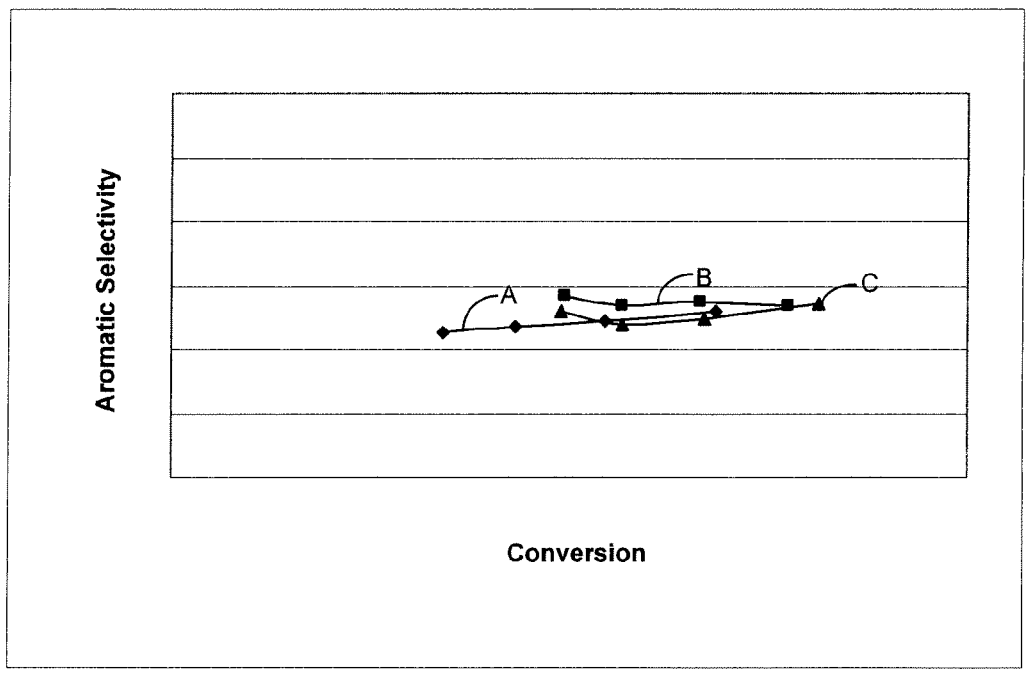
FIG. 3 is a plot of the total aromatic selectivity as a function of conversion as determined the comparative test rums of the Example.

Another consideration is whether the aromatic selectivity was effected by the presence of the water. FIG. 3 shows the total aromatic selectivity as a function of conversion. The two runs containing moisture in the feeds, Run B and Run C showed very similar aromatic selectivity compared to the non-moisture run, Run A. Therefore, aromatic selectivity is not reduced by including moisture in the feed.

The comparative data shows that the activity of the catalyst is higher in the present invention than is found in applications without water in the feed. Having water in the feed allows an operator to reduce the temperature of the dehydrocyclodimerization reaction zone and yet maintain the same conversion. Numerous benefits arise from increasing the activity, as discussed above; catalyst life is increased, capital costs may be reduced, throughput may be increased, and more.

What is claimed is:

1. A process for dehydrocyclodimerization comprising contacting, in a dehydrocyclodimerization zone at dehydrocyclodimerization conditions, a gallium-modified ZSM-5 catalyst bound with alumina containing phosphorus with a reaction mixture comprising aliphatic hydrocarbons having from 2 to 6 carbon atoms per molecule and from about 10 to about 100 wt. ppm water, or a water precursor in an amount resulting in from about 10 to about 100 wt. ppm water, and generating an aromatic product stream.

2. The process of claim 1 further characterized in that the ZSM-5 has a molar ratio of silicon per aluminum of greater than about 10 and a pore diameter of about 5-6 Angstroms.

3. The process of claim 1 further characterized in that the ZSM-5 comprises from about 30 to about 90 weight percent of the catalyst.

4. The process of claim 1 further characterized in that gallium comprises from about 0.1 to about 5 weight percent, as the metal, of the catalyst.

5. The process of claim 1 wherein the dehydrocyclodimerization conditions include a temperature from about 350° C. to about 650° C. (662° F. to 1202° F.), a pressure from about 0 to about 300 psi(g) (0 to 2068 kPa(g)), and a liquid hourly space velocity from about 0.2 to about 5 hr$^{-1}$.

6. The process of claim 1 wherein the dehydrocyclodimerization conditions include a temperature in the range from about 400° C. to about 600° C. (752° F. to 1112° F.), a pressure in or about the range from about 0 to about 150 psi(g) (0 to 1034 kPa(g)), and a liquid hourly space velocity of between 0.5 to 3.0 hr$^{-1}$.

7. The process of claim 1 further comprising adding from about 10 to about 100 wt. ppm water, or a water precursor in an amount resulting in from about 10 to about 100 wt. ppm water, to a feed fluid comprising aliphatic hydrocarbons having from 2 to 6 carbon atoms per molecule to generate the reaction mixture.

8. The process of claim 7 wherein the water or water precursor is added to the feed fluid using a liquid pump or vapor-vapor mixing.

9. The process of claim 1 wherein the dehydrocyclodimerization zone contains two or more reaction vessels and further comprising adding from about 10 to about 100 wt. ppm water, or a water precursor in an amount resulting in from about 10 to about 100 wt. ppm water, to an interstage feed fluid comprising aliphatic hydrocarbons having from 2 to 6 carbon atoms per molecule to generate the reaction mixture.

10. The process of claim 8 wherein the water or water precursor is added to the interstage feed fluid using a liquid pump or vapor-vapor mixing.

11. The process of claim 1 further comprising drying a feed fluid comprising aliphatic hydrocarbons having from 2 to 6 carbon atoms per molecule so that the feed fluid contains from about 10 to about 100 wt. ppm water, or a water precursor in an amount resulting in from about 10 to about 100 wt. ppm water in order to generate the reaction mixture.

12. The process of claim 1 further comprising partially drying the zeolitic catalyst so that the catalyst retains water or a water precursor in an amount resulting in from about 10 to about 100 wt. ppm water in the reaction mixture.

13. The process of claim 1 wherein the water precursor is selected from the group consisting of alcohols, ethers, aldehydes, phenols, ketones, and combinations thereof.

14. The process of claim 1 wherein the water precursor is selected from the group consisting of ethanol, methanol, butyl alcohol, dibutyl alcohol, tertiary butyl alcohol, and combinations thereof.

* * * * *